United States Patent [19]

Manzoni et al.

[11] Patent Number: 6,066,249
[45] Date of Patent: May 23, 2000

[54] METHOD FOR CALIBRATING AN INSTRUMENT FOR MEASURING ELECTROLYTES AND METABOLITES BY ANALYSIS OF BLOOD GASES

[75] Inventors: Angelo Manzoni; Roberto Daglio; Dario Frontini, all of Milan, Italy

[73] Assignee: Instrumentation Laboratory S.p.A, Milan, Italy

[21] Appl. No.: 09/056,464

[22] Filed: Apr. 7, 1998

[30] Foreign Application Priority Data

Apr. 15, 1997 [EP] European Pat. Off. ............. 97830175

[51] Int. Cl.⁷ .................................................. G01N 27/26
[52] U.S. Cl. ........................ 205/782; 204/415; 204/433; 205/783; 205/787.5; 436/11
[58] Field of Search ..................... 204/415, 431, 204/432, 433; 205/782, 782.5, 783, 787.5; 436/9.11

[56] References Cited

U.S. PATENT DOCUMENTS

| | | | |
|---|---|---|---|
| 4,116,336 | 9/1978 | Sorensen et al. | 436/11 |
| 4,424,276 | 1/1984 | Clark et al. | 436/50 |
| 4,960,708 | 10/1990 | Zowtiak et al. | 436/11 |
| 5,061,631 | 10/1991 | Calabrese | 436/11 |
| 5,789,253 | 8/1998 | Lauks et al. | 436/11 |

FOREIGN PATENT DOCUMENTS

| | | |
|---|---|---|
| 0 364 948 | 4/1990 | European Pat. Off. . |
| WO 94/06019 | 3/1994 | WIPO . |
| WO 96/28723 | 9/1996 | WIPO . |

OTHER PUBLICATIONS

EPO Search Report, Application No. EP 97 83 0175 (2 pgs.)

*Primary Examiner*—T. Tung
*Attorney, Agent, or Firm*—Testa, Hurwitz & Thibeault LLP

[57] ABSTRACT

A method for calibrating an instrument for the analysis of blood gases which possesses ion-sensitive electrodes and gas-sensitive electrodes and is used for the determination, in a biological fluid, of the concentration of electrolytes and metabolites in solution, and of the pH, $pO_2$ and $pCO_2$, the said calibration being carried out with at least one buffered solution containing $O_2$, a known or tonometer-measured amount of $CO_2$ and known concentrations of the electrolytes and metabolites to be determined, in which calibration the $pO_2$ titer is determined beforehand using atmospheric oxygen as reference.

11 Claims, No Drawings

METHOD FOR CALIBRATING AN INSTRUMENT FOR MEASURING ELECTROLYTES AND METABOLITES BY ANALYSIS OF BLOOD GASES

FIELD OF THE INVENTION

In its most general aspect, the present invention relates to a method for calibrating instruments for measuring the partial pressure of gases in liquid media, especially in biological fluids.

In particular, the present invention relates to a calibration method which may be applied to known measuring instruments, such as instruments for the analysis of blood gases, which are used to determine the partial pressure of oxygen and/or of carbon dioxide ($pO_2$ and $pCO_2$), as well as other components such as electrolytes, pH, metabolites, etc., in samples of biological fluid.

BACKGROUND OF THE INVENTION

Various instruments are known for the analysis of blood gases, these instruments ranging from ordinary routine apparatus to the most complex automated apparatus, which are used for the real-time monitoring of the levels of $pO_2$ and $pCO_2$ in the blood, along with other components, during surgical operations or intensive care.

These instruments, which operate at 37° C., comprise a series of specific electrochemical sensors for each individual determination, the sensors requiring frequent, if not continuous, calibration.

The term "electrochemical sensors" is understood to refer to potentiometric, amperometric or conductimetric systems which measure electroactive species in solution, either directly (electrolytic species) or indirectly (gases), by means of membranes which are selective for ions or gases respectively.

The ion-selective electrodes are calibrated using reference solutions, whereas the gas-selective electrodes may be calibrated using standardized gas mixtures, with ambient air or with reference liquids, the latter consisting of solutions equilibrated with gas mixtures at constant temperature.

The calibration of the gas-selective electrodes, in particular of the oxygen electrode used for the determination of the $pO_2$ in the blood, is of particular interest and many methods have been developed to carry out such a calibration.

The determination of the partial pressure of oxygen using instruments for the analysis of blood gases, which is carried out with a Clark amperometric electrode with which the $pO_2$ is determined in millimetres of mercury (mmHg), is known in the art.

In this case, calibration of the system takes place by recording the current signal of the oxygensensitive electrode at two known values of $pO_2$.

The first calibration point has a zero $pO^2$ value and is used to determine a base value.

The second calibration point, on the other hand, has a known $pO_2$ value which varies according to the type of instrument used and is between 100 and 200 mmHg.

This second calibration point serves to determine the slope of the calibration curve.

The first calibration point may be established in one of the following ways:

1) with a mixture of gases contained in a suitable cylinder having a zero concentration of oxygen;
2) with an aqueous solution containing a strongly reducing substance (sodium sulphite, sodium dithionite, etc.), in which the oxygen is chemically consumed;
3) using electrochemical methods which allow the oxygen to be removed by electrolysis;
4) by carrying out electrical zeroing on the instrument.

On the other hand, the second calibration point may be established in one of the following ways:

a) from a mixture of gases contained in a suitable cylinder with a known concentration of oxygen; by knowing the atmospheric pressure at which the measurement is taken, it is possible to obtain a known value of $pO_2$;
b) from atmospheric air in which the percentage of oxygen is constant (20.9%); in this case, also, it is necessary to know the atmospheric pressure when the measurement is taken;
c) with an aqueous solution equilibrated, when it is produced, with a gas mixture containing a suitable percentage of oxygen and packaged in collapsible, gas-impermeable containers;
d) with a solution equilibrated with atmospheric air at the same temperature as the measuring temperature (37° C.), with a stage of tonometry carried out directly on the instrument by bubbling or by passage through plastic, oxygen-permeable tubes or membranes; in this case, also, it is necessary to know the atmospheric pressure when the measurement is taken.

The methods listed above for establishing the second calibration point each have advantages and disadvantages.

Indeed, method a) has the advantage of being reliable, since a mixture of gases is used which is a standard controlled by extremely accurate gas-chromatographic reference methods.

Moreover, this allows the simultaneous calibration of the $pO_2$ and $pCO_2$ values.

However, this method has drawbacks associated with the use of compressed-gas cylinders, namely their bulk, safety problems and the difficulties involved in moving the instrument around.

Moreover, since the instruments also measure other parameters which require agents for calibrating in aqueous solution, it is necessary to carry out mixed cycles of calibration, partly with a gas mixture and partly with aqueous solutions, thereby considerably lengthening the time required to calibrate the instrument and/or complicating the fluid route.

Method b) for establishing the second calibration point has the advantage of using ambient air, which does not cost anything and has a constant composition, irrespective of location, thereby making it, de facto, a primary standard.

However, with ambient air, it is not possible to carry out the calibration for the determination of the $pCO_2$ and therefore instruments which use this method are coupled to a cylinder of carbon dioxide.

A variant of an instrument which uses the abovementioned method b) is the so-called Gas Mixer, in which mixtures of gases from air and from a cylinder of carbon dioxide are obtained directly from the instrument.

Lastly, method b) also necessarily uses mixed calibration cycles.

Method c) has the advantage over the preceding methods of being able to calibrate electrodes for gases and for electrolytes simultaneously, thus using shorter cycles without complicating the fluid route.

Moreover, the instrumentation is of minimal bulk since it does not require a cylinder, and the safety problems associated with the use of gas mixtures are also avoided.

However, this method suffers from the drawbacks associated with the use of tonometer-measured solutions.

Such solutions contain known dissolved amounts of oxygen and carbon dioxide together with known amounts of other components to be determined, such as bicarbonate, calcium, sodium, potassium, other ionic species and organic species such as glucose.

These solutions may be prepared in a tonometer by mixing the appropriate ingredients together so as to obtain a buffered solution and adding to this solution a gas mixture with a known titre of oxygen and carbon dioxide.

The gases and the aqueous phase equilibrate in the tonometer and the partial pressures of oxygen and of carbon dioxide are adjusted to the desired values.

These values correspond to molar concentrations which are considerably lower than the concentrations of these gases in the gas mixtures.

At this point, the solution thus prepared is stored in a gas-impermeable, collapsible sealed container which is generally a bag consisting of an aluminium laminate placed between layers of a thermoplastic polymer.

The solution may be sealed inside this bag at a gas pressure below atmospheric pressure, as described, for example, in U.S. Pat. No. 4,116,336, or above atmospheric pressure by also introducing a gas which diffuses rapidly, such as helium, into the bag, as described in U.S. Pat. No. 4,960,708.

In any case, calibration using these tonometer-measured solutions is almost always inaccurate as far as determining the $pO_2$ is concerned, since it has been found that the content of this gas in the bags tends to vary between the time they are prepared and the time they are used. The reason for this is that the metal layers of the bags are never totally impermeable to gases, especially to oxygen.

Moreover, the permeability of the gases may increase considerably, for example because the packaging is not completely leaktight and/or because of the possible exposure of the bags to high temperatures, with consequent degassing of the solution.

However, the abovementioned drawbacks essentially relate to variations in the $pO_2$ titre in the bag, since the $pCO_2$ titre tends to remain stable over time because of the intrinsic properties of the formulations of the solutions contained in the bags.

Moreover, the $pO_2$ titre in the bag may also decrease as a result of corrosion phenomena occurring in the metal layer of the containers with which the solution may come into contact during storage and/or because of microbiological contamination.

Consequently, the shelf-life of these solutions is also relatively short.

Method d) has essentially the same advantages as method c).

However, in this case also, the $pO_2$ titre of the solutions used is quite variable.

Moreover, the solution which is tonometer-measured with air cannot be used to calibrate the $pCO_2$ and the related instrumentation is quite complex and expensive, since it requires a thermostatically-controlled tonometry system.

Consequently, the calibration cycle is not the same for oxygen and the other parameters.

SUMMARY OF THE INVENTION

The problem which underlies the present invention is one of providing a method for calibrating an instrument for the analysis of blood gases, with which both gas-sensitive electrodes and ion-sensitive electrodes can be calibrated in a single cycle, which is reliable in its $pO_2$ determination and does not suffer from the drawbacks of the methods mentioned above.

This method must moreover be practical, safe, readily adaptable for routine purposes and should not require the use of gas cylinders.

The abovementioned problem is solved according to the present invention by means of a method for calibrating an instrument for the analysis of blood gases which possesses ion-sensitive electrodes and gas-sensitive electrodes and is used for the determination, in a biological fluid, of the concentration of electrolytes and metabolites in solution, and of the pH, $pO_2$ and $pCO_2$, the said method comprising the stages of:

provideng available at least one buffered calibration solution containing $O_2$ and a tonometer-measured or known amount of $CO_2$, the said solution moreover comprising known concentrations of the electrolytes and metabolites to be determined;

determining the $pO_2$ titre in at least one said calibration solution;

calibrating the electrodes in a single cycle with at least one said calibration solution in which the $pO_2$ titre has been determined;

wherein said stage of determining the $pO_2$ in at least one said calibration solution is carried out using atmospheric oxygen as reference.

The abovementioned method may advantageously also comprise a stage in which the electrodes are calibrated in order to determine a base value at zero oxygen content.

This calibration is performed by carrying out electrical zeroing on the instrument or by means of a calibration solution in which the oxygen has been removed by chemical or physical methods.

The biological fluid in which the electrolyte and metabolite concentrations are determined, together with the pH, $pO_2$ and $pCO_2$, may be blood, plasma, or serum.

Preferably, the electrolytes to be determined in the biological fluid are chosen from the group comprising sodium, potassium, lithium, calcium, magnesium and chloride ions and the metabolites to be determined are chosen from the group comprising glucose, lactate, urea, creatinine and pyruvate.

The aqueous solutions which may be used in the calibration method of the present invention are buffered solutions which contain oxygen and a known or tonometer-measured amount of carbon dioxide, the said solutions moreover comprising known concentrations of the electrolytes and metabolites to be determined.

Preferably, the abovementioned reference solutions contain known amounts of oxygen and carbon dioxide with $pO_2$ and $pCO_2$ measured by tonometer during production and are stored in collapsible, gas-impermeable containers.

The abovementioned solutions advantageously have a $pO_2$ of between 100 and 300 mmHg.

Given the constancy of the $O_2$ content of atmospheric air (20.9%), which is a consequence of the constancy of the average molecular weight of air, which is equal to 28.964 kg/KM up to an altitude of 86 km, the concept underlying the present invention was to use atmospheric air as primary standard for the determination of the exact $pO_2$ titre of the individual calibration solutions.

These determinations were expediently carried out before using the solutions to calibrate the electrodes.

In this way, in the calibration method of the present invention, the exact $pO_2$ titre is given to the individual bag containing the reference solution during installation on the instrument.

The value of the $pO_2$ titre of the bag determined against air is therefore used to calibrate the instrument and for all subsequent calibrations carried out alternately with blood samples.

The pO$_2$ titre of an individual bag is therefore determined only once or periodically, for example every day, depending on the times and conditions of use.

It was found, surprisingly, that determination of the pO$_2$ in blood samples upon implementation of the calibration method of the present invention gives very precise results and an accuracy which is comparable with that of similar determinations carried out by means of calibration with gas mixtures which, as has been seen, are reliable.

The calibration method of the present invention is therefore particularly advantageous since it has all the advantages of calibration with tonometer-measured solutions, in particular their convenience of use and their speed, and at the same time is also highly reliable with respect to the determination of pO$_2$ in biological fluids.

It clearly also allows the simultaneous determination of the pO$_2$ and pCO$_2$ in blood samples since, as has been mentioned previously, the pCO$_2$ of the bags tends to remain constant over time.

Moreover, the calibration cycle of the present invention is simple, rapid, particularly suitable for routine purposes and can easily be applied without the need for the specific instrumentation and most checks required in most conventional measuring equipment.

DETAILED DESCRIPTION OF THE INVENTION

The aims and advantages of the present invention will become more apparent from the description of the examples which follow, these being given by way of non-limiting guide.

EXAMPLE 1

Determination of the pO$_2$ Titre of a Tonometer-measured Calibration Solution.

In this example, the pO$_2$ titre of a tonometer-measured solution is determined, both against air and against a gas mixture containing 20.03% of O$_2$.

This solution is contained in a collapsible bag in which the oxygen content has been measured by tonometer during production and which contains the components listed in Table 1 below together with the respective concentrations in mmol/l:

TABLE 1

| Components of the tonometer-measured calibration solution | Concentration mmol/l |
|---|---|
| HEPES buffer | 50 |
| Sodium hydroxide | 26 |
| Sodium chloride | 9 |
| Potassium chloride | 5 |
| Sodium hydrogen carbonate | 25 |
| Calcium chloride | 1 |

The tonometer-measured solution moreover has a pH=7.38 at the measuring temperature (37° C.) and contains a suitable antimicrobial agent.

The following samples were placed in front of the oxygen electrode in an instrument for the analysis of blood gases operating at 37° C.:
- a gas mixture with a zero content of oxygen, in order to determine the zero response of the electrode;
- a gas mixture containing 20.03% of O$_2$;
- air;
- solution of tonometer-measured O$_2$.

The gas mixtures and the air were appropriately humidified before use at 37° C. for a period of 30 minutes and a water vapour pressure of 47 mmHg was measured at this temperature.

For each sample, the signals at the oxygen electrode were recorded in picoamperes (pA) at given times (1 minute after sampling).

The process carried out was as follows:

1) the response of the oxygen electrode for the mixture with a zero content of oxygen was determined by making three recordings of the signal in pA at the electrode and taking the average;

2) the signal in pA at the oxygen electrode for the gas mixture containing 20.03% of O$_2$ and for air were recorded;

3) the signal in pA at the oxygen electrode for the tonometer-measured solution was recorded.

Stages 2 and 3 are repeated so as to obtain three sets of values of the signals in pA at the electrode for each of the two determinations.

Lastly, the pO$_2$ values in mmHg of the solution were calculated both against the mixture containing 20.03% of O$_2$ and against air for each set of values of pA respectively and the average of the results obtained for each determination were taken.

CALCULATIONS pO$_2$ (M)=(759−47)*20.03/100=142.6 pO$_2$ air=(759−47)*20.9/100=148.8

$$pO_2(S\text{-}M) = \frac{\text{pA}(S) - \text{pA zero}}{\text{pA}(M) - \text{pA zero}} * 142.6$$

$$pO_2(S\text{-}A) = \frac{\text{pA}(S) - \text{pA zero}}{\text{pA air} - \text{pA zero}} * 148.8$$

where:

pO$_2$ (M)=partial pressure of oxygen in the gas mixture containing 20.03% of O$_2$, in mmHg;

pO$_2$ air=partial pressure of oxygen in the air, in mmHg;

pO$_2$ (S−M)=partial pressure of oxygen in the calibration solution against the gas mixture containing 20.03% of O$_2$, in mmHg;

pO$_2$ (S−A)=partial pressure of oxygen in the calibration solution against air, in mmHg;

pA (S)=picoamperes of the calibration solution;

pA (M)=picoamperes of the gas mixture containing 20.03% of O$_2$;

pA air=picoamperes of the air.

NOTES:

1) pA zero represents the average of three recordings of the signal in picoamperes at the oxygen electrode against a mixture with a zero content of oxygen: average value of three measurements=6.3 pA;

2) the barometric pressure during the experiment was 759 mmHg;

3) the water vapour pressure in the gas mixtures and in the air is 47 mmHg.

The results are presented in Tables 2 and 2b.

TABLE 2

Titration of tonometer-measured
solution against the gas
mixture containing 20.03% of O$_2$

| pA mixture containing 20.03% of O$_2$ | pA solution bag | pO$_2$ calculated for the solution (mmHg) |
|---|---|---|
| 708 | 717 | 144.4 |
| 703 | 713 | 144.6 |
| 700 | 711 | 144.9 |
|  | AVERAGE | 144.6 |

TABLE 2B

Titration of tenometer-measured solution
against air (20.9% O$_2$)

| pA air | pA solution bag | pO$_2$ calculated for the solution (mmHg) |
|---|---|---|
| 732 | 712 | 144.7 |
| 729 | 710 | 144.9 |
| 727 | 709 | 145.1 |
|  | AVERAGE | 144.9 |

As can be seen, the values obtained in the two tests are very similar.

EXAMPLE 2

Determination of the pO$_2$ in Tonometer-measured Blood Samples

In this example, the pO$_2$ in tonometer-measured blood samples was determined against a gas mixture containing 20.03% of O$_2$ and against the solution titrated against air of Example 1.

The tonometer-measured blood samples were prepared by means of the following process:

6 ml of fresh blood were placed in a tonometer at 37° C., in which a gas mixture having a known percentage of O$_2$, was bubbled through at atmospheric pressure the said mixture having been humidified beforehand at 37° C. for a period of 30 minutes.

At the end of this process, the value of the partial pressure of oxygen in the blood (theoretical pressure) was calculated in the following way:

theoretical pO$_2$=% O$_2$(M)*(P$_B$–P vapour 37° C.) where:
% O$_2$(M)=percentage of oxygen in the gas mixture;
P$_B$=barometric pressure during the experiment;
P vapour 37° C.=water vapour pressure at 37° C.

Three samples of blood having theoretical pO$_2$ values of 49.8 mmHg, 71.9 mmHg and 185.1 mmHg respectively were thus prepared.

The following samples were placed in front of the oxygen electrode in the instrument for the analysis of blood gases of Example 1:

a gas mixture with a zero content of oxygen, in order to determine the zero response of the electrode;
a gas mixture containing 20.03% of O$_2$;
the solution titrated against air of Example 1;
a tonometer-measured blood sample.

The gas mixtures and the air were appropriately humidified before use at 37° C. for a period of 30 minutes, and a water vapour pressure of 47 mmHg was read at this temperature.

For each sample, the signals at the oxygen electrode were recorded in picoamperes (pA) at given times (1 minute after sampling).

The process carried out was as follows:

1) the response of the oxygen electrode for the mixture with a zero content of oxygen was determined by making three recordings of the signal in pA at the electrode and taking the average;

2) the signal in pA at the oxygen electrode for the gas mixture containing 20.03% of O$_2$ and for the solution titrated against air of Example 1 were recorded;

3) the signal in pA at the electrode for the blood sample was recorded.

Stages 2 and 3 are repeated so as to obtain three sets of values of the signals in pA at the electrode for each determination.

Lastly, the pO$_2$ values in mmHg of the blood samples were calculated both against the mixture containing 20.03% of O$_2$ (Tables 3, 4 and 5) and against the solution titrated against air (pO$_2$ assigned 144.9 mmHg, Tables 3b, 4b and 5b) and for each determination the average of the results obtained was taken.

CALCULATIONS

The calculation carried out to obtain the value of pO$_2$ is the following:

$$pO_2(\text{blood-}M) = \frac{\text{pA blood} - \text{pA zero}}{\text{pA}(M) - \text{pA zero}} * pO_2(M)$$

$$pO_2(\text{blood-}S) = \frac{\text{pA blood} - \text{pA zero}}{\text{pA}(S) - \text{pA zero}} * pO_2(S)$$

where:

pO$_2$ (M)=partial pressure of oxygen in the gas mixture containing 20.03% of O$_2$,in mmHg;

pO$_2$ (S)=partial pressure of oxygen in the calibration solution titrated against air of Example 1, in mmHg;

pO$_2$ (blood-M)=partial pressure of oxygen in the blood sample against the gas mixture containing 20.03% of O$_2$, in mmHg;

pO$_2$ (blood-S)=partial pressure of oxygen in the blood sample against the calibration solution titrated again air of Example 1, in mmHg;

pA (S)=picoamperes of the solution titrated against air of Example 1;

pA (M)=picoamperes of the gas mixture containing 20.03% of O$_2$;

pA blood=picoamperes of the blood sample.

NOTES:

1) pA zero represents the average of three recordings of the signal, in picoamperes, at the oxygen electrode against a mixture with a zero content of oxygen: average value of three measurements=6.3 pA;

2) the barometric pressure during the experiment was 759 mmHg.

TABLE 3

$pO_2$ measurement in blood measured
by tonometer at 37° C. ($O_2$ = 7.00%)
against a gas mixture containing 20.03%
$O_2$ ($pO_2$ = 142.6 mmHg)
Theoretical $pO_2$ value in the blood:
49.8 mmHg pA zero used: 6.3 pA

| pA af mixture containing 20.03% of $O_2$ | pA of tonometer-measured blood | $pO_2$ calculated for the blood (mmHg) |
|---|---|---|
| 699 | 254.4 | 51.0 |
| 700 | 244.1 | 48.9 |
| 704 | 241.1 | 48.0 |
|  | AVERAGE | 49.3 |

TABLE 3B $pO_2$ measurement in blood measured
by tonometer at 37° C. ($O_2$ = 7.00%)
against a solution titrated against air
($pO_2$ = 144.9 mmHg)
Theoretical $pO_2$ value in the blood:
49.8 mmHg pA zero used: 6.3 pA

| pA of solution | pA of tonometer-measured blood | $pO_2$ calculated for the blood (mmHg) |
|---|---|---|
| 712 | 234.4 | 46.8 |
| 710 | 234.4 | 47.0 |
| 711 | 233.3 | 46.7 |
|  | AVERAGE | 46.8 |

TABLE 4

$pO_2$ measurement in blood measured
by tonometer at 37° C. ($O_2$ = 10.1%)
against a gas mixture containing 20.03%
$O_2$ ($pO_2$ = 142.6 mmHg)
Theoretical $pO_2$ value in the blood:
71.9 mmHg pA zero used: 12.6 pA

| pA af mixture containing 20.03% of $O_2$ | pA of tonometer-measured blood | $pO_2$ calculated for the blood (mmHg) |
|---|---|---|
| 717 | 338 | 64.9 |
| 716 | 339 | 66.2 |
| 714 | 343 | 67.2 |
|  | AVERAGE | 66.1 |

TABLE 4B $pO_2$ measurement in blood measured
by tonometer at 37° C. ($O_2$ = 10.1%)
against a solution titrated against air
($pO_2$ = 144.9 mmHg)
Theoretical $pO_2$ value in the blood:
71.9 mmHg pA zero used: 12.6 pA

| pA of solution | pA of tonometer-measured blood | $pO_2$ calculated for the blood (mmHg) |
|---|---|---|
| 722 | 333 | 65.4 |
| 721 | 332 | 65.3 |
| 720 | 333 | 65.6 |
|  | AVERAGE | 65.4 |

TABLE 5

$pO_2$ measurement in blood measured
by tonometer at 37° C. ($O_2$ = 26%)
against a gas mixture containing 20.03%
$O_2$ ($pO_2$ = 142.6 mmHg)
Theoretical $pO_2$ value in the blood:
185.1 mmHg pA zero used: 22.2 pA

| pA af mixture containing 20.03% of $O_2$ | pA of tonometer-measured blood | $pO_2$ calculated for the blood (mmHg) |
|---|---|---|
| 720 | 871 | 173.5 |
| 719 | 868 | 173.1 |
| 719 | 878 | 175.1 |
|  | AVERAGE | 173.9 |

TABLE 5B $pO_2$ measurement in blood measured
by tonometer at 37° C. ($O_2$ = 26%)
against a solution titrated against air
($pO_2$ = 144.9 mmHg)
Theoretical $pO_2$ value in the blood:
185.1 mmHg pA zero used: 22.2 pA

| pA of solution | pA of tonometer-measured blood | $pO_2$ calculated for the blood (mmHg) |
|---|---|---|
| 733 | 869 | 172.6 |
| 732 | 870 | 173.1 |
| 731 | 866 | 172.5 |
|  | AVERAGE | 172.7 |

Analysis of the tables reveals that the $pO_2$ values obtained for the blood samples against the tonometer-measured calibration solution (Tables 3b, 4b and 5b) are comparable with those obtained against the gas mixture (Tables 3, 4 and 5).

Consequently, the calibration method of the present invention is reliable for the determination of the $pO_2$ in a biological fluid.

This determination is both faster and easier than that carried out using the standard method for gas mixtures.

What we claim is:

1. A method for calibrating an instrument for the analysis of blood gases which possesses a gas-sensitive electrode and is used for the determination, in a biological fluid, of $pO_2$ and $pCO_2$, comprising the steps of:

providing at least one buffered calibration solution containing $O_2$ and a known amount of $CO_2$;

determining the $pO_2$ titre in said calibration solution; and calibrating the electrode in a single cycle with said calibration solution in which the $pO_2$ titre has been determined;

wherein said step of determining the $pO_2$ in said calibration solution uses atmospheric oxygen as a reference.

2. A method according to claim 1, further comprising the step of calibrating the electrode by determining a signal from the electrode when the electrode is detecting a $pO_2$ of zero.

3. A method according to claim 2 wherein the electrode is calibrated to a $pO_2$ of zero by a method selected from the group consisting of electrical zeroing of the instrument, chemically removing oxygen to form a zero $pO_2$ calibration solution, and physically removing oxygen to form a zero $pO_2$ calibration solution.

4. A method according to claim 2, wherein the step of determining $pO_2$ titre comprises:

determining $pO_2$ in the atmosphere by subtracting a water vapour pressure from a barometric pressure and multiplying the result by a percentage of $O_2$ in the atmosphere;

measuring an electrical signal of a solution with no $O_2$;

measuring an electrical signal of the calibration solution;

measuring an electrical signal of the atmosphere;

subtracting the electrical signal of the solution with no $O_2$ from the electrical signal of the calibration solution to obtain a value for the calibration solution above a background level;

subtracting the electrical signal of the solution with no $O_2$ from the electrical signal of the atmosphere to get a value for the atomsphere above a background level; and dividing the signal for the atomsphere above background from the signal for the calibration solution above background, and multiplying the result by the $pO_2$ of the atmosphere.

5. Method according to claim 1, wherein said biological fluid is chosen from the group comprising blood, plasma and serum.

6. A method according to claim 1, further comprising the step of determining in the biological fluid a concentration of at least one electrolyte selected from the group consisting of sodium, potassium, lithium, calcium, magnesium and chloride ions.

7. Method according to claim 1, wherein the $pO_2$ in said at least one calibration solution is between 100 and 300 mmHg.

8. Method according to claim 1, wherein said at least one calibration solution contains known amounts of oxygen and carbon dioxide with $pO_2$ and $pCO_2$ measured by tonometer during production and is stored in collapsible, gas-impermeable containers.

9. Method according to claim 8, wherein the tonometer-measured $pO_2$ of the said calibration solution is between 100 and 300 mmHg.

10. A method according to claim 1, wherein the step of determining the $pO_2$ of the calibration solution occurs immediately after an installation of the calibration solution to the instrument.

11. A method according to claim 1, further comprising the step of determining in the biological fluid a concentration of at least one metabolite selected from the group consisting of glucose, lactate, urea, creatinine and pyruvate.

* * * * *